United States Patent
Dittmer et al.

(10) Patent No.: US 9,841,421 B2
(45) Date of Patent: Dec. 12, 2017

(54) SENSOR DEVICE FOR MAGNETICALLY ACTUATED PARTICLES

(75) Inventors: Wendy Uyen Dittmer, Eindhoven (NL); Mikhail Mikhaylovich Ovsyanko, Eindhoven (NL); Toon Hendrik Evers, Eindhoven (NL); Jeroen Hans Nieuwenhuis, Waalre (NL); Joannes Baptist Adrianus Dionisius Van Zon, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1140 days.

(21) Appl. No.: 13/988,833

(22) PCT Filed: Nov. 28, 2011

(86) PCT No.: PCT/IB2011/055341
§ 371 (c)(1),
(2), (4) Date: Aug. 14, 2013

(87) PCT Pub. No.: WO2012/073182
PCT Pub. Date: Jun. 7, 2012

(65) Prior Publication Data
US 2014/0057366 A1   Feb. 27, 2014

(30) Foreign Application Priority Data

Nov. 30, 2010 (EP) .................................... 10193083

(51) Int. Cl.
*G01N 33/543* (2006.01)
*G01N 27/82* (2006.01)
(Continued)

(52) U.S. Cl.
CPC ..... *G01N 33/54373* (2013.01); *G01N 21/274* (2013.01); *G01N 21/552* (2013.01);
(Continued)

(58) Field of Classification Search
CPC ..... B60T 8/1703; B60T 8/171; B64C 25/426; B64C 25/42; B64D 45/00; G01N 27/72;
(Continued)

(56) References Cited

U.S. PATENT DOCUMENTS 7,314,763 B2   1/2008   Song
7,508,200 B2   3/2009   Kahlman
(Continued)

FOREIGN PATENT DOCUMENTS

GB    2078968 A    6/1980
WO    2005010542 A2    2/2005
(Continued)

*Primary Examiner* — Melanie Y Brown

(57) ABSTRACT

The invention relates to a sensor device (100) and a method for the detection of magnetic particles (1) in a sample chamber (2) with a contact surface (11). The sensor device (100) comprises a sensor unit (120, 130) for detecting magnetic particles (1) in a target region (TR) and/or in at least one reference region on the contact surface. Moreover, it comprises a magnetic field generator (140) for generating a magnetic field that shall guide magnetic particles to the contact surface. With the help of these components, an "auxiliary parameter" is determined that is related to the magnetic particles (1) and/or their movement but that is independent of binding processes taking place in the target region between magnetic particles and the contact surface. The auxiliary parameter may for example be related to the degree of mismatch between the positions reached by the magnetic particles (1) under the influence of a magnetic field and the target region (TR). The evaluation results can be used to validate and/or correct the measurements obtained in the target region (TR).

18 Claims, 9 Drawing Sheets

(51) Int. Cl.
*G01N 27/72* (2006.01)
*G01N 27/74* (2006.01)
*G01N 35/00* (2006.01)
*G01N 21/27* (2006.01)
*G01N 21/552* (2014.01)

(52) U.S. Cl.
CPC ............ *G01N 27/72* (2013.01); *G01N 27/745* (2013.01); *G01N 27/825* (2013.01); *G01N 33/54326* (2013.01); *G01N 35/0098* (2013.01)

(58) Field of Classification Search
CPC ............... G01N 27/745; G01N 27/845; G01N 33/54326; G01N 33/0098
USPC ......................................................... 436/526
See application file for complete search history.

(56) References Cited

U.S. PATENT DOCUMENTS

| | | | |
|---|---|---|---|
| 2002/0090320 A1* | 7/2002 | Burow | B01L 9/523 422/64 |
| 2004/0120185 A1* | 6/2004 | Kang | G01N 27/76 365/158 |
| 2006/0088444 A1 | 4/2006 | Gambini | |
| 2008/0218165 A1* | 9/2008 | Kahlman | G01N 33/54326 324/260 |
| 2009/0104707 A1* | 4/2009 | Wang | G01N 33/54326 436/86 |
| 2009/0206832 A1* | 8/2009 | Kahlman | B82Y 25/00 324/252 |
| 2009/0219012 A1* | 9/2009 | Nieuwenhuis | B82Y 25/00 324/204 |
| 2009/0227044 A1 | 9/2009 | Dosev | |
| 2010/0060265 A1 | 3/2010 | Nieuwenhuis | |
| 2010/0092996 A1* | 4/2010 | Verschuren | G01N 21/552 435/7.1 |
| 2010/0324828 A1* | 12/2010 | Kahlman | B82Y 25/00 702/19 |

FOREIGN PATENT DOCUMENTS

| | | |
|---|---|---|
| WO | 2005010543 A1 | 2/2005 |
| WO | 2005111614 A1 | 11/2005 |
| WO | 2008/072156 * | 6/2008 |
| WO | 2008/102218 * | 8/2008 |
| WO | 2008142492 A1 | 11/2008 |
| WO | 2008155716 A1 | 12/2008 |
| WO | 2008155723 A1 | 12/2008 |
| WO | 2009004538 A1 | 1/2009 |
| WO | 2009027726 A1 | 3/2009 |
| WO | 2009040712 A2 | 4/2009 |
| WO | 2009115951 A1 | 9/2009 |
| WO | 2009125356 A1 | 10/2009 |
| WO | 2010044005 A2 | 4/2010 |

* cited by examiner

SENSOR DEVICE FOR MAGNETICALLY ACTUATED PARTICLES

FIELD OF THE INVENTION

The invention relates to a sensor device and a method for the detection of magnetic particles in a sample chamber, wherein said particles are guided by a magnetic field towards a contact surface.

BACKGROUND OF THE INVENTION

From the WO 2008/155716 A1 a biosensor is known in which target components labeled with magnetic beads are detected by frustrated total internal reflection (FTIR) at the sensing surface of a cartridge. The described biosensor is particularly designed and suited for point-of-care applications, for example roadside drug tests.

SUMMARY OF THE INVENTION

Based on this background it was an object of the present invention to provide means for detecting magnetic particles in a sample chamber with improved accuracy and/or reliability of the detection results.

This object is achieved by a sensor device according to claim 1 and a method according to claim 2. Preferred embodiments are disclosed in the dependent claims.

According to its first aspect, the invention relates to a sensor device for the detection of magnetic particles in a sample chamber, wherein said sample chamber has a contact surface at which magnetic particles can collect. The term "magnetic particles" shall comprise both permanently magnetic particles as well as magnetizable particles, for example superparamagnetic beads. The size of the magnetic particles typically ranges between 3 nm and 50 µm. Moreover, the magnetic particles may comprise bound target components (e.g. biomolecules) one is actually interested in. The "sample chamber" is typically an empty cavity; it may be an open cavity, a closed cavity, or a cavity connected to other cavities by fluid connection channels. The sensor device comprises the following components:

a) A sensor unit for detecting magnetic particles in (at least a part of) a sub-region of the contact surface that will be called "target region" in the following. Additionally alternatively, the sensor unit may be adapted to detect magnetic particles in at least one further sub-region of the contact surface, said further sub-region being called "reference region" in the following. It should be noted that the sensor unit may comprise several sub-units or may be a unique device (as long as separate detection of magnetic particles in the target region and the reference region(s) is provided). The sensor unit may for example generate an optical image comprising both the target region and the reference region(s), wherein separate parts of this image are individually processed.

b) A magnetic field generator for generating a magnetic field within the sample chamber, wherein said magnetic field shall guide magnetic particles in its reach towards the contact surface (i.e. to at least one sub-region of the contact surface). The magnetic field will typically have a nonzero gradient that allows to exert magnetic forces on magnetic (dipole) particles.

c) An evaluation unit for determining from the detection signals of the sensor unit an "auxiliary parameter" that is related to the magnetic particles and/or to their movement within the sample chamber (i.e. their movement through the medium in the sample chamber) but that is independent of binding processes taking place in the target region between magnetic particles and the contact surface. A typical binding process taking place in the target region is for example the covalent binding of magnetic particles to the contact surface, though other types of binding (e.g. via hydrogen bonds) shall be comprised, too. The evaluation unit may be realized in dedicated electronic hardware, digital data processing hardware with associated software, or a mixture of both. It is usually coupled to the sensor unit (and optionally also to the magnetic field generator) for receiving signals from it and/or for controlling it.

The invention further relates to an associated method for the detection of magnetic particles in a sample chamber with a contact surface at which magnetic particles can collect, wherein said method comprises the following steps:

a) Generating a magnetic field within the sample chamber that shall guide magnetic particles to the contact surface.

b) Detecting magnetic particles in (at least a part of) a target region on the contact surface and/or in at least one reference region on the contact surface.

c) Determining from the detection signals obtained in step b) for the reference region and/or the target region an auxiliary parameter that is related to the magnetic particles and/or their movement but that is independent of binding processes taking place in the target region between magnetic particles and the contact surface.

The method comprises in general form the steps that can be executed with a sensor device of the kind described above. Reference is therefore made to the above description of the sensor device for more information on the details of said method.

The sensor device and the method described above have the advantage that they provide, additionally to the usual measurement in a target region, an "auxiliary parameter" that is related to the magnetic particles and/or their movement but that is independent of binding processes taking place in the target region between magnetic particles and the contact surface. The auxiliary parameter can therefore provide valuable background information about circumstances that may affect the outcome of the "actual measurements" in the target region, i.e. of measurements that crucially depend on processes (like binding) occurring between magnetic particles and the contact surface.

In the following, various preferred embodiments of the invention will be described that relate both to the sensor device and the method described above.

According to one embodiment of the invention, the magnetic field that is generated in the sample chamber shall guide magnetic particles specifically to the target region, and the auxiliary parameter is related to the mismatch between the positions actually reached by the magnetic particles and the target region. As there is usually a huge number of magnetic particles in a sample and as the magnetic field will usually not be restricted to certain sub-regions of the sample chamber, there will in general always be some particles that reach the target region and others that do not. The evaluation unit may hence quantify the auxiliary parameter (i.e. the mismatch between the reached positions and the target region) for example as the percentage of all magnetically actuated particles that reach the target region. Furthermore, the auxiliary parameter may preferably be derived from detection signals of both the target region and at least one reference region.

With the help of the aforementioned auxiliary parameter, the sensor device and the method allow for the (automatic) verification if magnetic particles of a sample are correctly guided by a magnetic field. This is a significant advantage for the following reasons: The detection result in the target region is usually the signal one is actually interested in, providing for example information about the presence and/or amount of a certain target component within the sample (said target component may e.g. be a molecule labeled with a magnetic bead). If there is, for whatever reason, a misalignment between the magnetic field and the target region, less magnetic particles will reach the target region, giving rise to an underestimation of the amount of magnetic particles in the sample. This impairment of the measurement results can be prevented by the described sensor device and method because they allow to verify the correct arrival of magnetic particles in the target region.

According to a further development of the aforementioned embodiment, at least one reference region is disposed at a position outside the target region. In case of a proper particle guidance, the detection signals for such a reference region should be zero or at least below a given threshold.

In another embodiment, there is at least one reference region that (partially or completely) overlaps with the target region. Such a reference region will be reached by properly guided magnetic particles. Zero or too low detection signals for this reference region will therefore indicate an incorrect particle guidance.

Of course any combination of the mentioned arrangements of reference regions can be used, comprising some reference regions that overlap with and other reference regions that are distinct from the region reached by properly guided magnetic particles.

In another embodiment of the invention, a reference region may at least partially surround the target region. In the above case in which properly guided magnetic particles shall reach the target region, the detection signal in such a reference region will normally be zero. A displacement of magnetic particles in the direction of the reference region can however be detected (here and in the following, the "displacement of magnetic particles" is a shortcut for the more precise "displacement of the positions reached by actuated magnetic particles"). If the reference region completely surrounds the target region, a displacement in any direction can be detected.

The sample chamber in which the sample with magnetic particles is provided may be located in an exchangeable cartridge, i.e. in a standalone component separate from the sensor device. Due to its contamination with a sample, such a cartridge will usually be a disposable item, made for example from plastics by injection moulding.

According to another embodiment of the invention, there are at least two reference regions disposed at different sides of the target region. Preferably, a plurality of reference regions is distributed around the target region in such a way that any misalignment between magnetic particles and the target region can be discovered as magnetic particles will reach at least one of the reference regions. In a further development of the embodiment with several reference regions, the detection signals from different reference regions are individually evaluated. Such an individual evaluation allows for example to determine in which direction magnetic particles are displaced with respect to the target region. This information can for instance be exploited to adjust the setup. An individual evaluation of detection signals from different reference regions may further be used to determine an auxiliary parameter that is related to a possible clustering of magnetic particles. Clustering produces chains of magnetic particles in the direction of the magnetic field lines, which typically causes an anisotropy in the distribution of magnetic particles. This anisotropy can be detected with the help of several reference regions.

In a practically important case, the target region may comprise a binding (sub-)region with binding sites at which magnetic particles can specifically bind. The binding sites may for example be molecules (e.g. antigens) that specifically bind to the magnetic particles (e.g. to antibodies comprised by the magnetic particles). Specific binding of magnetic particles to the binding sites is then a typical example of a process the auxiliary parameter shall be independent of. Preferably, there is no overlap between the binding region and the reference region(s) (otherwise binding processes may have an influence on the detection signals in the reference regions; if the auxiliary parameter measures the correct guidance of magnetic particles, reference regions with binding sites might for example show an increasing concentration of magnetic particles not indicative of the correct guiding of particles to the target region).

According to another preferred embodiment of the invention, the auxiliary parameter is related to the amount of magnetic particles (irrespective if they are linked to a target component or not) in the sample chamber. Such an auxiliary parameter may particularly be expressed as a concentration of the magnetic particles, i.e. an amount per unit volume. In a typical assay for the detection of target components in a sample, the concentration of all magnetic particles in a sample chamber and the concentration of target components determine together the amount of magnetic particles that will first bind to a target component and then bind to a binding region (via said target components). The total amount of magnetic particles in the sample chamber is hence of the same importance on the outcome of such an assay as the concentration of target components itself. It is therefore tried to always introduce a well known, constant amount of magnetic particles to an assay. Determining an auxiliary parameter that corresponds to the amount of magnetic particles allows to verify if this important precondition is actually fulfilled or not.

In another important embodiment, the determined auxiliary parameter is related to a possible clustering of magnetic particles. Clustering of magnetic particles is usually induced by a magnetic field, which makes the particles line up in chains along the magnetic field lines. Such clusters may sometimes persist even after the magnetic field has been switched off. For various reasons, this (irreversible) clustering of magnetic particles can affect the measurement results in the target region. Detection of clustering via the determined auxiliary parameter can therefore help to improve the measurement results.

According to a further embodiment, the determined auxiliary parameter may comprise the viscosity of the medium in the sample chamber, i.e. the medium through which the magnetic particles must migrate towards the contact surface. For reasons of efficiency, the time needed for an essay should be as short as possible. To achieve correct measurement data, enough magnetic particles must however reach the contact surface of the sample chamber in the available time. As this requirement is inter alia determined by the migration velocity of the magnetic particles, which in turn depends on the viscosity of the surrounding medium, knowledge of the viscosity can provide valuable information about the reliability of an assay.

In still another embodiment, the determined auxiliary parameter may be related to the magnetic field that is generated within the sample chamber and that shall guide the magnetic particles to the contact surface. In particular, the strength, the homogeneity, and/or the alignment of the magnetic field with the target region may be represented by the auxiliary parameter. In this way another parameter with crucial influence on the detection results in the target region may be verified.

In another embodiment, the determined auxiliary parameter may represent a redispersion condition of magnetic particles. Redispersion of magnetic particles may for instance take place at the beginning of an assay, when a (sample) liquid contacts a supply of dried magnetic particles. Redispersion may further take place during an assay when clusters of magnetic particles dissolve. The auxiliary parameter may for example indicate the percentage of magnetic particles that have dissolved into the liquid from a previously dried state.

In still another embodiment, the determined auxiliary parameter may be related to the spatial distribution of magnetic particles. Such a parameter may for instance represent the concentration of magnetic particles within the sample chamber or a part of it.

Of course a combination of all the above mentioned auxiliary parameters and/or further auxiliary parameters may be determined within the same assay, too. As will be apparent from the detailed description of embodiments of the invention, it is also possible to derive a plurality of different auxiliary parameters from one and the same measurement in the target region and/or the reference region(s), thus gaining various insights from a single measurement.

The magnetic field that shall guide the magnetic particles to the contact surface may preferably be modulated, for example be pulsed (i.e. switched on and off in a repetitive manner). In case of a pulsed magnetic field, the frequency of the repetitive switching-off of the magnetic field preferably ranges between about 10 Hz and about 0.1 Hz (wherein the period of this switching is defined as the time between two consecutive switching-on events). The duty cycle of the repetitive switching-off of the magnetic field preferably ranges between about 5% and about 90%, wherein said duty cycle is defined as the duration of the "on" interval with respect to the whole switching period (comprising both the "on" and "off" interval). Via the duty cycle it can be controlled how much time the magnetic particles have to freely migrate without the influence of a magnetic field.

The mentioned modulation of the magnetic field typically induces a modulation of the detection signals obtained in the target region and/or the reference region(s), respectively. It turns out that these modulated detection signals may have some characteristics that provide additional information. The auxiliary parameter may therefore optionally be determined from detection signals recorded during the action of the modulated magnetic field.

In a first concrete example of the aforementioned approach, the auxiliary parameter is determined from the local amplitude occurring in the recorded detection signals, i.e. the difference between a local maximum and the neighboring local minimum of the detection signal obtained in a reference region or in the target region. Said local maxima and minima of the detection signal typically occur synchronous to the pulsation of the magnetic field. As an example, the (total) amount of magnetic particles in the sample chamber may be inferred from such local amplitudes.

In a second concrete example, the auxiliary parameter is determined from the shape of pulses of the recorded signal (in the target region and/or the reference region(s)). Experiments show that the shape of signal pulses which are induced by a modulated magnetic field are particularly sensitive to a clustering of magnetic particles. More generally, the modulated magnetic field generates modulated detection results for the reference regions that distinguish, in case of an (irreversible) particle clustering, with respect to amplitude, rate of change, and/or phase.

According to another embodiment of the invention, the auxiliary parameter is determined from the rate of change (or slope) of the recorded signal (in the target region and/or the reference region(s)). This rate of change may be determined as an average during certain periods (e.g. during periods a pulsed magnetic field is on), or as the rate of change during a particular phase of an assay, for example during the first period the magnetic field is switched on. It turns out that this auxiliary parameter can particularly provide information about the viscosity of a sample.

In another embodiment of invention, the auxiliary parameter is derived from a comparison of the detection signals in the target region and the reference region(s). If both of the target region and the reference region are within the reach of the generated magnetic field, the comparison between the associated detection signals may for example yield an auxiliary parameter related to the homogeneity of said field. If at least one reference region is outside the intended reach of the magnetic field, a comparison may yield information about the proper alignment between the magnetic field and various regions on the contact surface. Such an information about a proper alignment of the magnetic field may particularly be important if the sample chamber is disposed in an exchangeable cartridge.

The auxiliary parameter obtained by the evaluation of detection signals may be exploited in different ways. According to one possibility, an (optical, acoustic etc.) alarm signal is generated (by the evaluation unit or an additional alarm unit) if the auxiliary parameter happens to lie outside a given range that is considered as "normal". As an example, the auxiliary parameter may e.g. measure the mismatch between the positions reached by the magnetic particles and the target region. If then say less than 90% (or less than 60%, or 50%) of the magnetic particles reach the target region, this may be considered as a (significant) mismatch justifying the emission of an alarm signal. When an alarm signal is issued, the user may decide how to react, for example by discarding the whole measurement, by adjusting the setup (e.g. improving the alignment between magnetic particles and target region), by making a control measurement or the like.

In another embodiment, the detection results representing the (amount of) magnetic particles in the target region are corrected according to the determined auxiliary parameter. This approach requires that some relation (a "calibration") between the auxiliary parameter and the outcome of the measurement in the target region is known, which may then be exploited to correct the measurements. As an example, the auxiliary parameter may e.g. measure the degree of mismatch between the positions reached by the magnetic particles and the target region (the "degree of mismatch" being expressed e.g. as the percentage of magnetic particles NOT reaching the target region; the parameter should be a scalar and not only be a binary value ("mismatch/no-mismatch")). If then for example only X % of the magnetic particles reach the target region, a linear relation between mismatch and detection results would imply that the detection results are only X % of their proper value. Hence the measurement should be corrected by a factor 100/X.

The detection of magnetic particles in the target region and/or the reference region(s) may optionally be achieved with an optical, magnetic, mechanical, acoustic, thermal and/or electrical sensor element. A magnetic sensor element may particularly comprise a coil, Hall sensor, planar Hall sensor, flux gate sensor, SQUID (Superconducting Quantum Interference Device), magnetic resonance sensor, magneto-restrictive sensor, or magneto-resistive sensor of the kind described in the WO 2005/010543 A1 or WO 2005/010542 A2, especially a GMR (Giant Magneto Resistance), a TMR (Tunnel Magneto Resistance), or an AMR (Anisotropic Magneto Resistance). An optical sensor element may particularly be adapted to detect variations in an output light beam that arise from a frustrated total internal reflection due to magnetic particles at a sensing surface. In another embodiment, the optical sensor element may be adapted to directly detect light scattered by magnetic particles.

The invention further relates to the use of the sensor device described above for molecular diagnostics, biological sample analysis, chemical sample analysis, food analysis, and/or forensic analysis. Molecular diagnostics may for example be accomplished with the help of magnetic beads or fluorescent particles that are directly or indirectly attached to target molecules.

BRIEF DESCRIPTION OF THE DRAWINGS

These and other aspects of the invention will be apparent from and elucidated with reference to the embodiment(s) described hereinafter. These embodiments will be described by way of example with the help of the accompanying drawings in which.

Like reference numbers or numbers differing by integer multiples of 100 refer in the Figures to identical or similar components.

DESCRIPTION OF PREFERRED EMBODIMENTS

The invention will in the following be described with respect to the optical detection of magnetic particles in a bio sensor, though other detection principles and/or applications are possible as well.

The described embodiments of the invention have in common that they comprise (i) means (sensor unit) for detecting magnetic particles in a target region on the contact surface of a sample chamber and/or in at least one reference region, and (ii) a magnetic field generator for generating a magnetic field that shall guide magnetic particles to the contact surface. With the help of these components, an "auxiliary parameter" is determined that is related to the magnetic particles and/or their movement but that is independent of binding processes taking place in the target region between magnetic particles and the contact surface.

Two particular approaches that apply the aforementioned principle will be described in more detail, a first approach with respect to FIGS. 1 to 5, and a second approach with respect to FIGS. 6 to 17.

Figure 1:
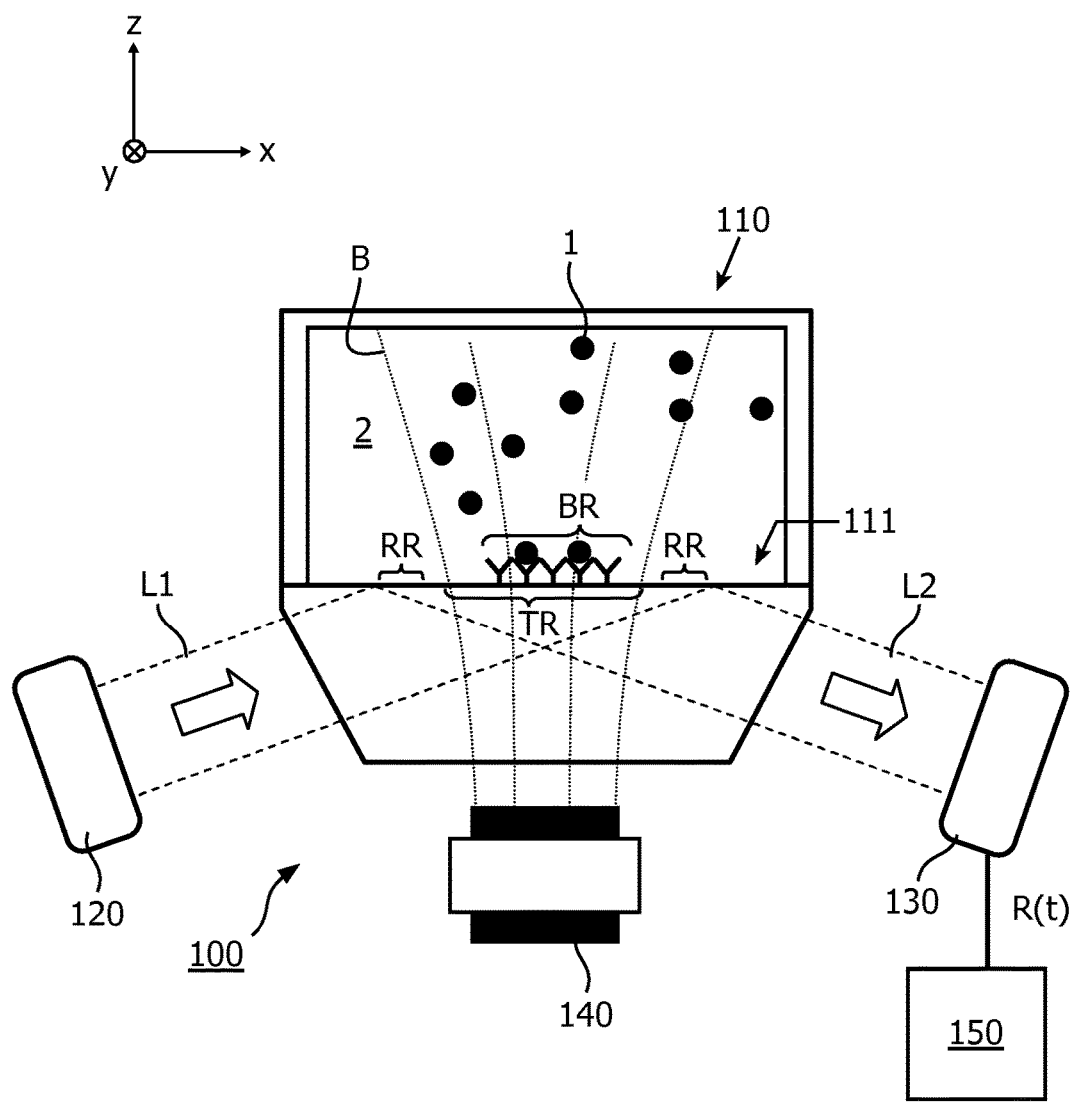
FIG. 1 schematically shows a side view of a first sensor device according to the present invention in which magnetic particles in a cartridge are detected by frustrated total internal reflection (FTIR) and in which a misalignment between the positions reached by the magnetic particles and a target region is detected.

FIG. 1 shows an exemplary sensor device 100 according the first approach. The sensor device 100 comprises a light source 120 for emitting an "input light beam" L1, a light detector 130 for detecting and measuring an "output light beam" L2, and an evaluation unit 150 which is coupled to the light detector (and optionally also to other components of the sensor device) and receives detection signals R(t) therefrom. The input light beam L1 is emitted into a (disposable) carrier or cartridge 110 that may for example be made from glass or transparent plastic like poly-styrene. The cartridge 110 comprises a sample chamber 2 in which a sample fluid with target components to be detected (e.g. drugs, antibodies, DNA, etc.) can be provided. The sample further comprises magnetic particles 1, for example super-paramagnetic beads, wherein these particles 1 are usually bound as labels to the aforementioned target components (for simplicity only the magnetic particles 1 are shown).

The (bottom) interface between the cartridge material and the sample chamber 2 is formed by a "contact surface" 111. This contact surface 111 is preferably coated in at least one binding region BR with capture elements, e.g. antibodies, which can specifically bind the target components on the magnetic particles 1.

The sensor device 100 further includes a magnetic field generator, for example comprising an electromagnet 140 with a coil and a core (and further magnets not shown in the Figure), for controllably generating a magnetic field B at the contact surface 111 and in the adjacent space of the sample chamber 2. With the help of this magnetic field B, the magnetic particles 1 can be manipulated, i.e. be magnetized and particularly be moved (if magnetic fields with gradients are used). Thus it is particularly possible to attract magnetic particles 1 to a "target region" TR on the contact surface 111.

The light source 120 may comprise an LED, e.g. a red 650 nm LED, that generates the input light beam L1 which is transmitted into the cartridge 110. The input light beam L1 arrives at the contact surface 111 at an angle larger than the critical angle of total internal reflection (TIR) and is therefore totally internally reflected as the output light beam L2. The area covered by the input light beam L1 comprises both the target region TR as well as adjacent "reference regions" RR that will be explained in more detail below. The output light beam L2 leaves the cartridge 110 through another surface and is detected by the light detector, e.g. by the light-sensitive pixels of a camera 130.

While the magnetic field B is drawn in FIG. 1 only within the target region TR, it should be noted that its reach will typically have no sharp boundary, i.e. the field will also be present (with a lower field strength) in the neighboring reference regions RR. Practically, there will in fact be very limited space in the miniaturized cartridge 110 where there is absolutely no magnetic field.

The described sensor device 100 applies optical means for the detection of magnetic particles 1 and the target components one is actually interested in. For eliminating or at least minimizing the influence of background (e.g. of the sample fluid, such as saliva, blood, etc.), the detection technique should be surface-specific. As indicated above, this is achieved by using the principle of frustrated total internal reflection. This principle is based on the fact that an evanescent wave propagates (exponentially dropping) into the sample 2 when the incident light beam L1 is totally internally reflected. If this evanescent wave then interacts with another medium having a different refractive index from water like the magnetic particles 1, part of the input light will be coupled into the sample fluid (this is called "frustrated total internal reflection"), and the reflected intensity will be reduced (while the reflected intensity will be 100% for a clean interface and no interaction). Further details of this procedure may be found in the WO 2008/155723 A1, which is incorporated into the present text by reference.

The sensor device 100 described so far can for example be used for rapid, sensitive and easy-to-use molecular diagnostics, designed to detect biological targets labeled with magnetic particles. As an example, the sensor device 100 may realize a sensitive, 5-minute point-of-care (POC) test for cardiac troponin I (cTnI). This test is a one-step sandwich immunoassay performed in a stationary liquid in which all assay processes are integrated by the use of magnetic forces acting on magnetic nanoparticle labels. In the first phase of the assay, nanoparticles highly loaded with antibody move through the sample solution for effective troponin molecule capture. Subsequently actuating magnets 140 are engaged to move and transport the particles with high speed to the sensor surface 111 for binding. Thereafter, a sequence of finely tuned magnetic pulses is applied to facilitate optimal binding and mixing of the nanoparticles containing cTnI molecules at the antibody functionalized surface in the binding region BR. After the particles react in the binding region BR, free and non-specifically bound particles are rapidly removed with a magnetic wash by applying a magnetic field oriented away from the detection surface. Seamless integration of the assay steps facilitate the design of a simple, single-chamber cartridge, in which dry-reagents, including magnetic particles are deposited.

Tests of the described kind are often aimed for use by non-technical personnel. It is desirable to reject test results from tests that have not been performed correctly for whatever reason. Furthermore, fail-safe mechanisms are especially important if the test is to be used to make clinical decisions in emergency and critical situations, e.g. as a test for the diagnosis of heart attacks.

An important type of failure occurs when magnetic particles redisperse and are not optimally placed (via magnetic attraction) above the binding region BR where the assay occurs. This is often a consequence of the misalignment of the cartridge 110 containing the contact surface 111 relative to the magnets 140. The magnetic particles as a result are collected by the magnets over a region on the contact surface that is inactive.

FIGS. 2a-c show in this respect a top view onto the contact surface 111 of the cartridge 110 from FIG. 1. Four different regions to be distinguished are shown:

1. The binding region BR which comprises binding sites for magnetic particles (with target molecules) and which is star-shaped in this embodiment. The actual measurement is done within this binding region with an associated sensor unit. In the sensor device 100, this is realized by evaluating the pixels corresponding to the binding region BR in the image generated by the camera 130.

2. A "target region" TR which represents the desired positions to which magnetic particles shall be guided by the attractive forces of the magnet 140. As shown in the example, the target region TR typically covers the binding region BR.

3. "Reference regions" RR in which separate detection of magnetic particles is possible. In the sensor device 100, this is realized by separately evaluating the pixels corresponding to the reference regions RR in the image generated by the camera 130.

4. A region PG actually hit by the cloud or group of magnetic particles under the effect of the attractive forces of the magnet 140. It should be noted that in practice magnetic particles will reach the contact surface also outside the shown region PG because the cloud of magnetic particles as well as the magnetic field will usually have fuzzy boundaries. Hence the region PG may more properly be defined as the part of the contact surface where the concentration of magnetic particles from the cloud is between a given percentage (e.g. 30%) and 100% of its maximum.

In FIG. 2a, the case of a severe misalignment of the cartridge 110 and the magnet 140 is shown. The region PG actually hit by the magnetic particles has no overlap with the target region TR, let alone with the binding region BR.

FIG. 2b illustrates the frequent case of a slight misalignment (on the order of 50 micron) such that there are magnetic particles over the target region TR, but the highest concentration of particles is not over the binding region BR. This leads to an assay signal result that is lower than expected. Based on this signal a different concentration of analyte might be extracted from the calibration curve than what is the actual concentration, giving an incorrect result.

FIG. 2c illustrates the case of a correct alignment, in which all magnetic particles are properly guided to the target region TR.

In order to deal with the cases of misalignment shown in FIGS. 2a and 2b, it is proposed to detect magnetic particles in at least one "reference region" RR outside the binding region BR while particles are brought to the contact surface 111 with the magnet 140 and detected in the binding region BR using a technique sensitive to the presence of particles at the surface, preferably frustrated total internal reflection (FTIR). It is preferred to use an array of several reference regions RR to map the exact location of the magnetic particle grouping PG relative to the binding spot BR, i.e. to determine an "auxiliary parameter" that represents the mismatch between the positions reached by the magnetic particles and the target region. The measured signals in the reference regions RR obtained when particles are attracted to the surface 111 indicate the distribution of particle density in the grouping.

The reference regions RR can have the following properties:

a) All regions are outside the target region TR expected to be occupied by the particle mass.

b) All regions are inside the target region TR expected to be occupied by the particle mass.

c) Some regions are inside and some are outside the target region TR expected to be occupied by the particle mass.

It should be noted that the "target region TR expected to be occupied by the particle mass" will usually imply or require some definition with respect to the term "expected", because in practice there will be no sharp boundaries of the regions reached by magnetic particles. Hence it may for example be defined that the target region TR shall be occupied by 90% of the whole particle mass in case the magnetic particles have been properly guided.

Figure 2:
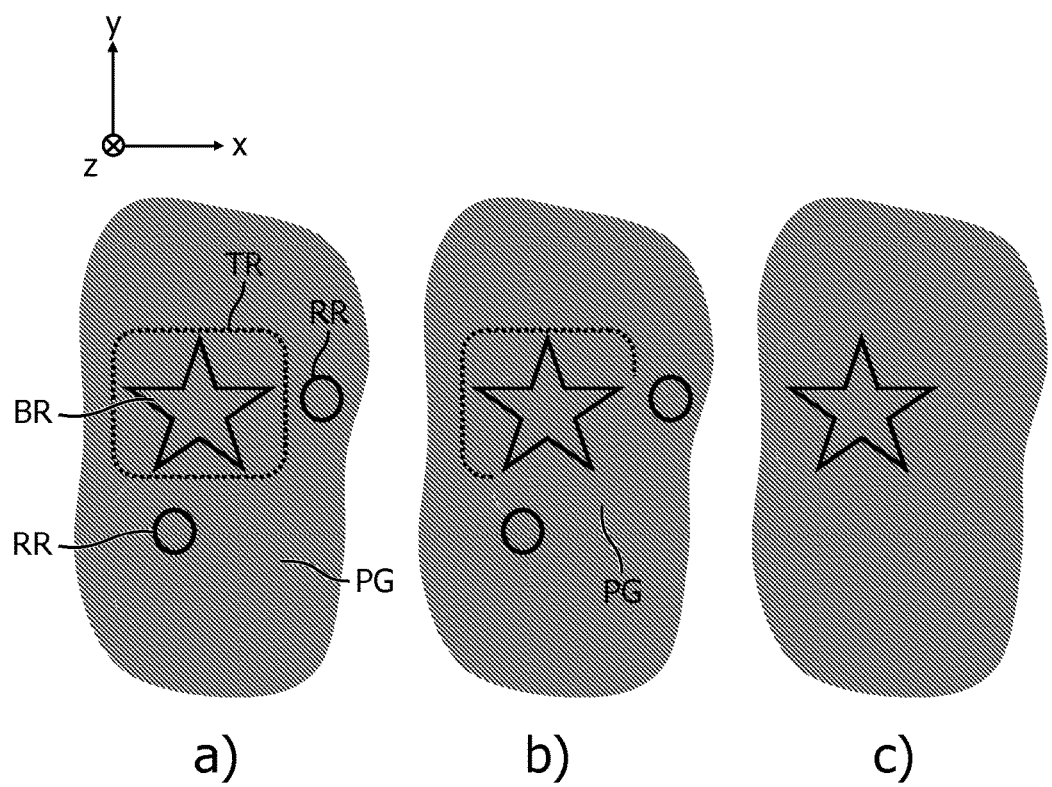
FIG. 2 shows a view onto the contact surface of the sample chamber of FIG. 1, illustrating (a) a complete misalignment, (b) a partial misalignment, and (c) a perfect alignment of magnetic particles and target region.

In the first alternative a), which is shown in FIG. 2, all reference regions RR are measured outside the area expected to be occupied by the particle mass, i.e. outside the target region TR. A low signal should be observed in all these regions indicative of the absence of significant amounts of particle. Depending on the proximity of these reference regions RR relative to the binding spot BR and the extent of the particle grouping PG, the detection of a significant signal in one of these reference regions RR can indicate a major misalignment (e.g. small particle grouping and reference regions far from binding regions) or a slight misalignment (e.g. large particle grouping and reference regions close to binding regions).

Figure 6:
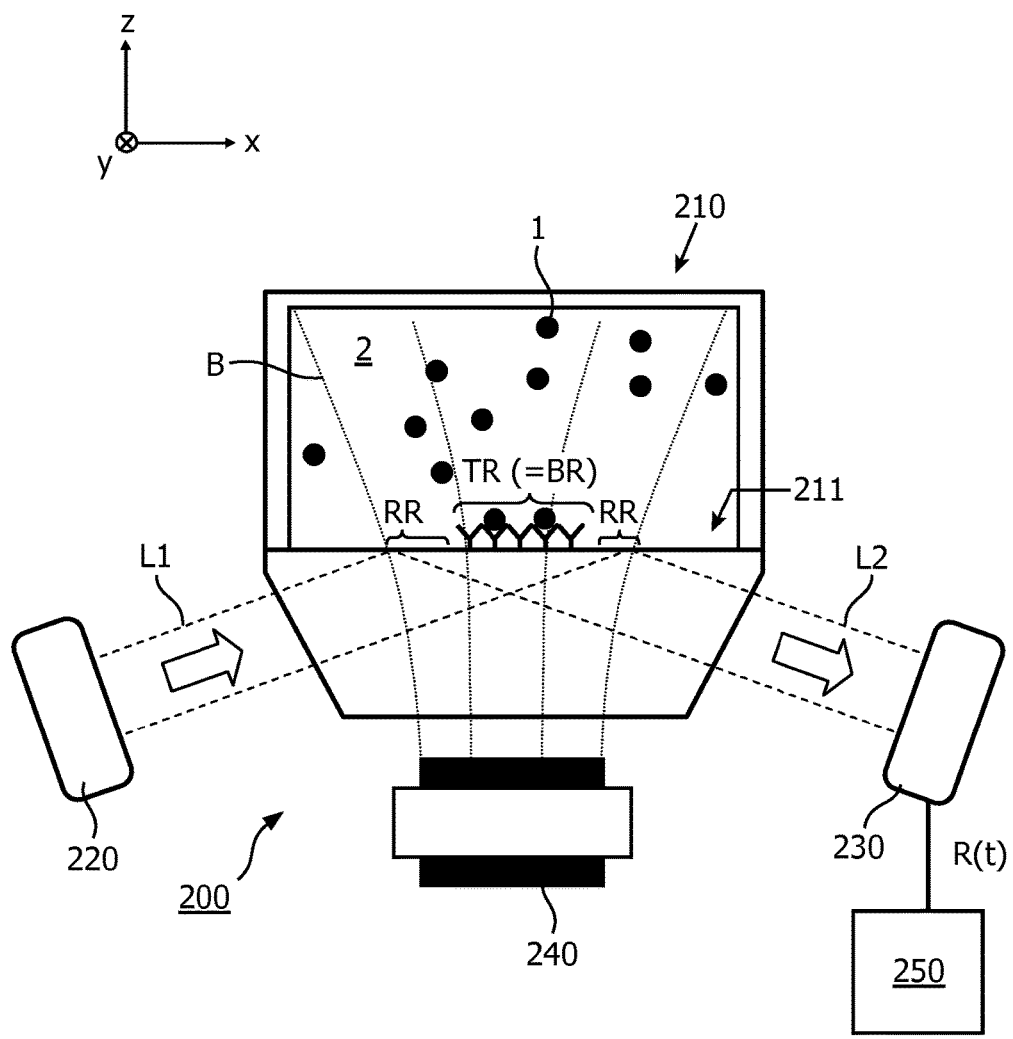
FIG. 6 schematically shows a side view of a second sensor device according to the present invention in which magnetic particles in a cartridge are detected by frustrated total internal reflection (FTIR) and in which detection results are obtained for a target region and at least one reference region that are both in the reach of a magnetic field.

In the second alternative b), all reference regions are measured inside the area expected to be occupied by the particle mass, i.e. inside the target region. A detectable signal should be observed in all these regions indicative of the amount particle reaching the contact surface. Depending on the proximity of these reference regions relative to the binding spot and the extent of the particle grouping, the reduction of the signal in one of these reference regions below a certain threshold value can indicate a misalignment. It may be noted that FIG. 6 shows an embodiment of this alternative b) (provided that the target region TR indicated there is extended to comprise also the adjacent reference regions RR).

In another embodiment, the signal amplitude, rate of signal change, and/or signal phase differences between the different reference regions can be used as an auxiliary parameter related to the monodispersity of the magnetic particles reaching the contact surface 111. The signals from the particles, if they are monodisperse, follow the magnetic field lines. If the particles are clustered (due to interference from the sample proteins, faulty redispersion, degradation of the reagents etc.), they generate a different signal distribution over the reference regions.

Figure 3:
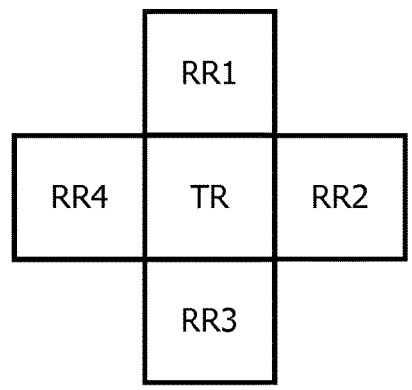
FIG. 3 illustrates the relative arrangement of reference regions and target region for the measurements shown in FIGS. 4 and 5.
Figure 4:
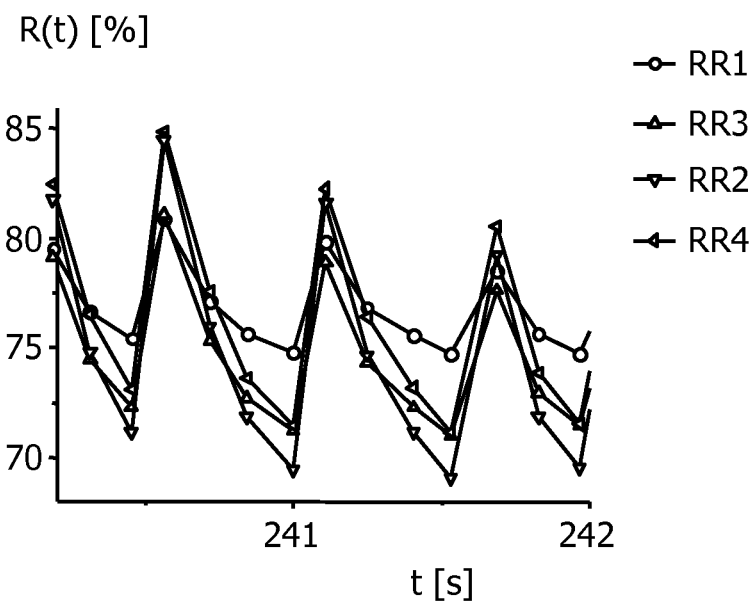
FIG. 4 shows the detection results in the four reference regions of FIG. 3 in case of a modulated magnetic field and a monodisperse sample.
Figure 5:
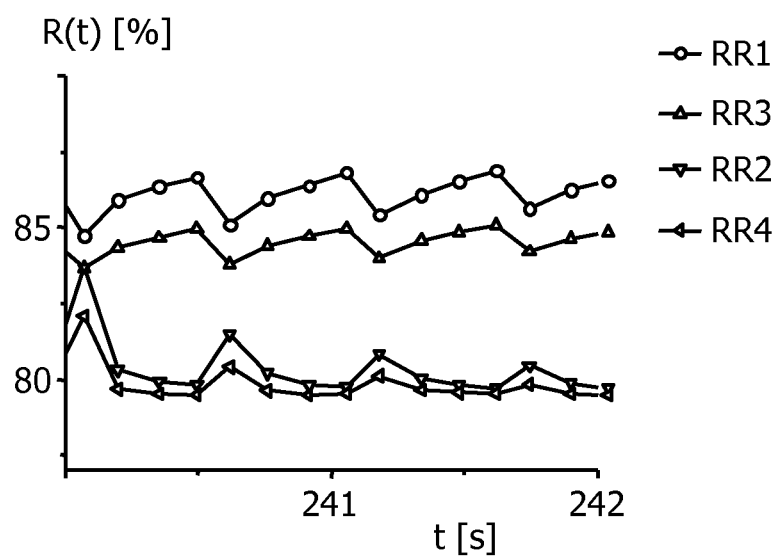
FIG. 5 shows how the detection results of FIG. 4 change in case of a clustered sample.

The aforementioned situation is illustrated in the example of FIGS. 3 to 5, in which a sample containing clusters is compared with a monodisperse sample. The diagrams in FIGS. 4 and 5 show detection signals (vertical axis: FTIR signal R(t) in relative units; horizontal axis: time t) of the signal from magnetic particles (500 nm) that are repeatedly brought to the contact surface using a magnetic field and released. The detection signals are obtained from the four reference regions RR1, RR2, RR3, and RR4 defined outside of the target region TR as shown in FIG. 3. For a monodisperse sample (FIG. 4), the signals over all four reference regions overlap. Whereas for the clustered sample (FIG. 5), the signals in the horizontal reference regions (RR2, RR4) differ substantially from the vertical regions (RR1, RR3) both in amplitude and in phase. This can be attributed to the field lines which have a different out of sensor plane component in the x and y directions such that particles are at different distance from the contact surface based on the location. When the magnetic field is turned off, the particles redisperse homogeneously and move towards the surface. In the case of the clusters, the clusters do not redisperse and it requires more time for the clusters further away to reach the surface, hence the inhomogeneity in reference signal distribution is observed.

In summary, the first approach described above with respect to FIGS. 1 to 5 comprises a robust reference measurement to determine the orientation of the colloidal magnetic particle mass in solution relative to a binding surface in an affinity based-assay. The aim is to determine whether the colloidal mass is at the optimal location for generating high assay signals. The reference measurement is to be performed in real time and simultaneously under the same conditions as the actual assay to give information about the correct functioning of the actual assay. If at any phase during the assay completion, deviations in the optimal orientation occur, the analyzer can be designed to reject the results given for the actual assay and automatically indicate test failure.

FIGS. 6 to 17 illustrate a second approach in which auxiliary parameters according to the principles of the present invention are determined.

FIG. 6 shows an exemplary sensor device 200 that can be used in the second approach. As the sensor device 200 is mainly identical to the sensor device 100 of FIG. 1, reference is made to the above description with respect to the common components like the cartridge 210, the light source 220, the light detector 230, and the magnet 240. The main difference with respect to the previous embodiment is that the magnetic field B which acts on magnetic (nano-) particles or beads 1 in the sample chamber 2 now extends over both a target region TR and adjacent reference regions RR (if present). This means that magnetic beads 1 are attracted to both the target region TR and the reference regions RR. Moreover, the target region TR is in this embodiment congruent with the "binding region" BR that is covered with binding sites (e.g. antibodies that are specific to target components on the magnetic particles 1). A further difference are the procedures that can be executed by the evaluation unit 250, as will be explained below.

Again it should be noted in this context that the magnetic field B will in practice have no sharp boundary. Hence a proper definition of the "extension" of the magnetic field will require the provision of some threshold (e.g. in terms of a normalized field strength) below which a point in space is considered as being field-free. Moreover, the field strength may vary between and/or within the target region TR and the reference regions RR. For example, most of the magnetic particles will usually be directed to the target region TR while less are directed to the reference regions RR. Hence it is not necessary that the magnetic particles are equally attracted to both the target region TR and the reference regions RR, as long as there is a correlation between the auxiliary parameter and the outcome of the actual measurements.

Figure 7:
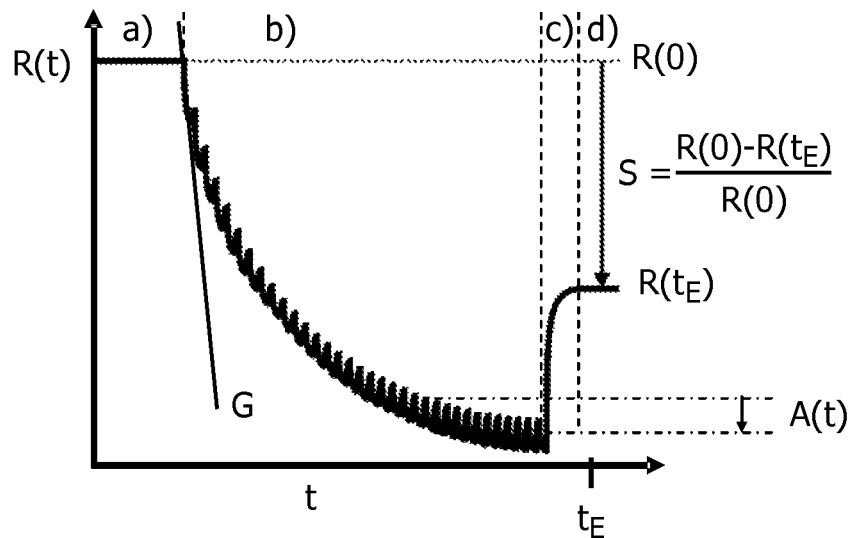
FIG. 7 schematically shows a typical FTIR detection signal R recorded with the sensor device of FIG. 6 in the target region.

When using the sensor device 200 for a sandwich immunoassay with magnetic particles, the signal R(t) (=reflected FTIR light intensity) recorded by the light detector 230 for the target region TR may look as displayed in FIG. 7. The following phases can be distinguished in this diagram:

a) A phase of redispersion of magnetic beads and of incubation.

b) An attraction phase during which magnetic beads are attracted to the contact surface 211 by a pulsed magnetic field B. Magnetic particles with a bound target may bind during this phase to the binding sites in the target/binding region TR.

c) A washing phase during which non-bound particles are removed from the contact surface 211.

d) A detection phase in which the "signal change" S is determined that represents the final amount of magnetic particles bound to the target region TR.

As can be seen by the oscillations in the (raw) signal R(t), the magnetic particles are generally attracted in a pulsed manner using the electromagnet 240. These oscillations are mainly caused by magnetic particles entering the evanescent field but not binding to the surface; therefore they can leave the evanescent field again when the magnets attracting the beads to the contact surface are switched off and optionally a (top) magnet (not shown) directing the beads away from the surface is switched on. As indicated in the diagram of FIG. 7, a "local amplitude" A(t) can be defined as the difference between the local maximum and the local minimum of the signal R(t) that are nearest to a considered time point t.

In the described procedure, the assay performance is dependent on numerous factors besides the analyte concentration. These factors comprise for example the actuation protocol (which is in turn influenced by the positions of the magnets, the strength of the magnetic field etc.), the total amount of magnetic particles available in the sample chamber, the homogeneity of the redispersion of the magnetic particles, the aggregation (clustering) state of the magnetic particles, the amount and functionality of the antibodies on the particles (tracer antibodies) and on the sensor surface (capture antibodies), and many other factors.

In the development of an assay, much effort is put into minimizing the variations in all these factors, such that from the final assay result S the concentration of the analyte can be accurately determined. However, when any of the aforementioned factors is different than expected (e.g. if one of the magnets is not functioning, if the amount of magnetic particles in a particular cartridge deviates, or if the particles are clustering) this can lead to wrong assay results, which can have severe consequences. It is therefore important that the sensor device performing the assay is able to detect such deviations, preferably by means of control mechanisms that require little or no additional development and are able to detect many deviations in the assay simultaneously.

In the following several proposals will be described how information about various aspects of an assay can be extracted from the signals that are recorded. This information can be expressed as an "auxiliary parameter" and used in mainly two ways:

As a control: If one aspect of the assay displays a deviation of the auxiliary parameter above a certain threshold, the measurement is disqualified and the sensor device returns an error message. This is very important to exclude false negatives.

As a calibrator: When it is know how a particular deviation in the auxiliary parameter leads to an altered interaction of magnetic particles with the surface (and therefore an altered end signal S), it is possible to correct for this effect and e.g. multiply the result of the signal change S with a factor dependent on the amount of deviation.

As the variations/oscillations in the detection signal R obtained for the target region TR and/or the reference regions RR are dependent on the amount of magnetic particles 1 entering and leaving the evanescent field, analyzing these oscillations can give important information about:

the total amount of magnetic particles 1 in the sample chamber;

the aggregation state (clustering) of magnetic particles;

the correct redispersion of the magnetic particles;

the strength of the magnetic field B;

the homogeneity of the magnetic field B;

the viscosity of the liquid in the sample chamber.

Figure 8:
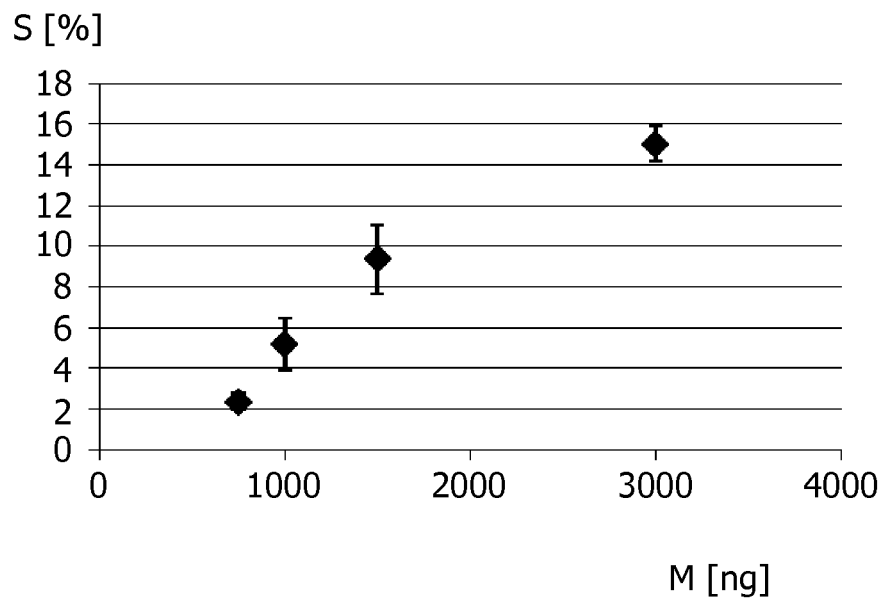
FIG. 8 is diagram showing the FTIR signal change S obtained in the target region for the detection of 100 pM cTnI using different amounts M of magnetic beads.

As a first example, FIG. 8 shows in a diagram the signal change S obtained in the binding region BR for the detection of 100 pM cardiac troponin I (cTnI) using different total amounts M of magnetic particles 1 in the sample chamber 2 (the amount M comprises magnetic particles irrespective if they are bound to a target component or not; for the definition of the signal change S, see FIG. 7). The diagram shows that the assay performance is clearly dependent on the amount M of magnetic beads used in the assay.

Figure 9:
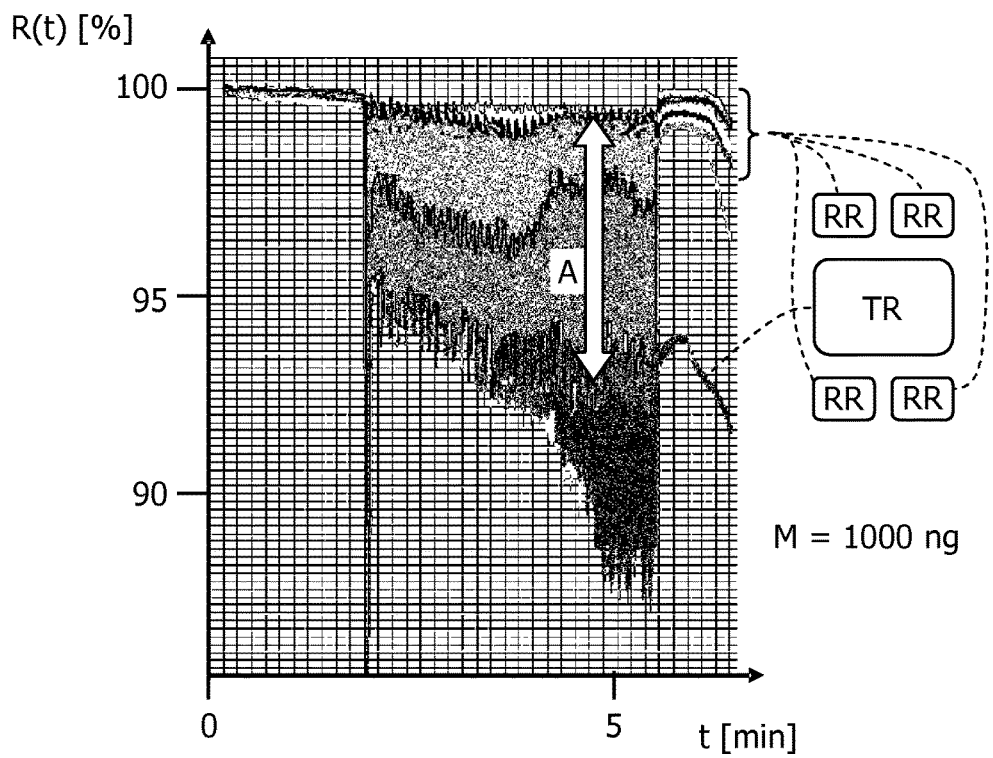
FIG. 9 illustrates the recorded FTIR detection signals R in the target region and in reference regions during the detection of 100 pM cTnI using 1000 ng magnetic beads.
Figure 10:
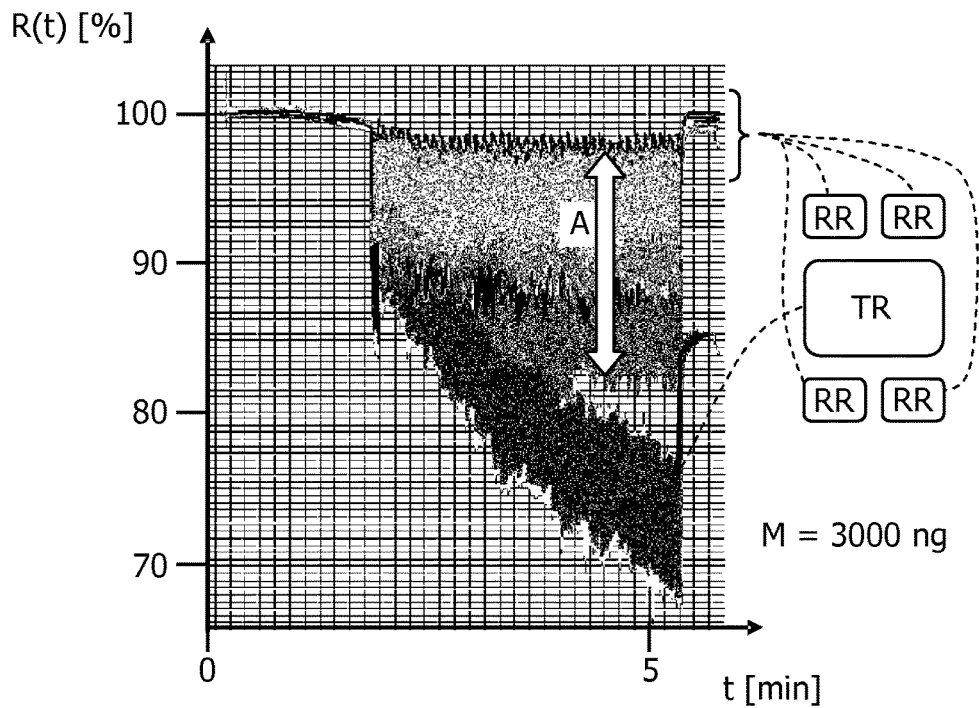
FIG. 10 illustrates the recorded FTIR detection signals R in the target region and in reference regions during the detection of 100 pM cTnI using 3000 ng magnetic beads.

FIGS. 9 and 10 additionally show two screenshots of raw signals R(t) (relative units) recorded in the target region TR and the reference regions RR for total amounts of M=1000 ng (FIG. 9) and M=3000 ng (FIG. 10) of magnetic particles. The arrangement of the target region TR and the four reference regions RR these signals are derived from are indicated in the right part of the Figures (e.g. the lowest curve in both FIGS. 9 and 10 displays the signal detected in the binding spot TR, whereas the other curves show particles entering the evanescent field in reference regions RR next to the spot). These data also show that the total amount M of magnetic particles in the assay has a clear influence on the amount of magnetic particles interacting with the contact surface. For example, the (local) amplitude A (as defined in FIG. 7) of the signal measured in an area next to the binding spot is clearly lower for a lower amount of particles.

Figure 11:
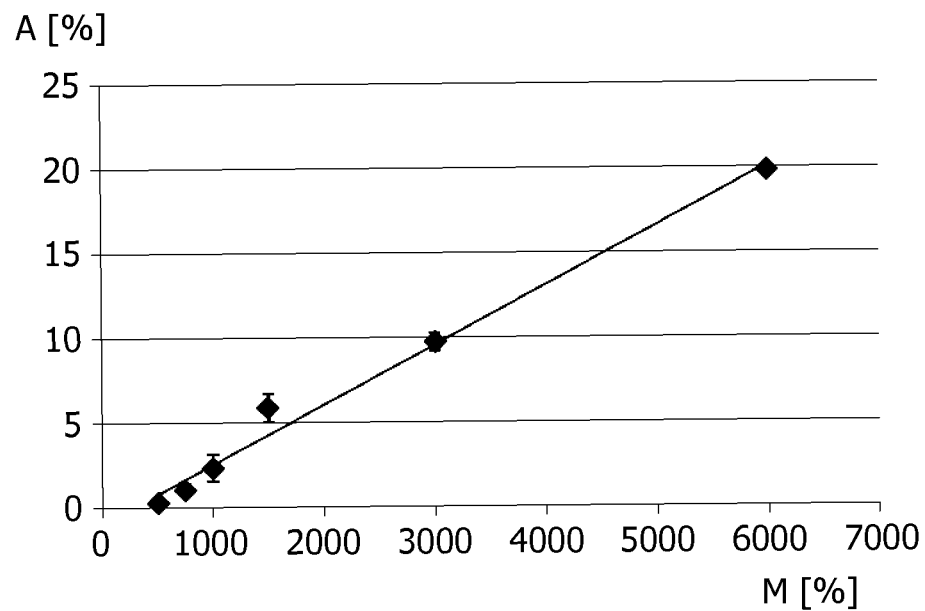
FIG. 11 shows the average signal amplitude A measured between 3 and 4 minutes of assays as shown in FIGS. 9 and 10 for different amounts M of magnetic beads used in the assay.

FIG. 11 illustrates how the amplitude of the signal in the reference regions RR is dependent on the total amount M of magnetic particles in the assay. In particular, the diagram shows the average signal amplitude A measured between 3 and 4 minutes of the assay as shown in FIGS. 9 and 10 obtained for different amounts M of magnetic particles. Furthermore, each data point is the average of three repetitions; error bars represent the standard deviation.

As can be seen in FIG. 11, the total amount M of magnetic particles can be accurately measured using the signal amplitude A. The signal amplitude A can hence serve as an "auxiliary parameter" that is related to the magnetic particles (namely to their total amount) but that is independent of processes (namely a binding) taking place in the target region. If an amplitude A (whether measured in a reference region RR or in the binding region TR/BR itself) deviates from an expected value, this could be used to disqualify the measurement, i.e. the finally measured signal change S in the target region TR. However, the amplitude A could also be used as a calibrator to correct the obtained value S.

Figure 12:
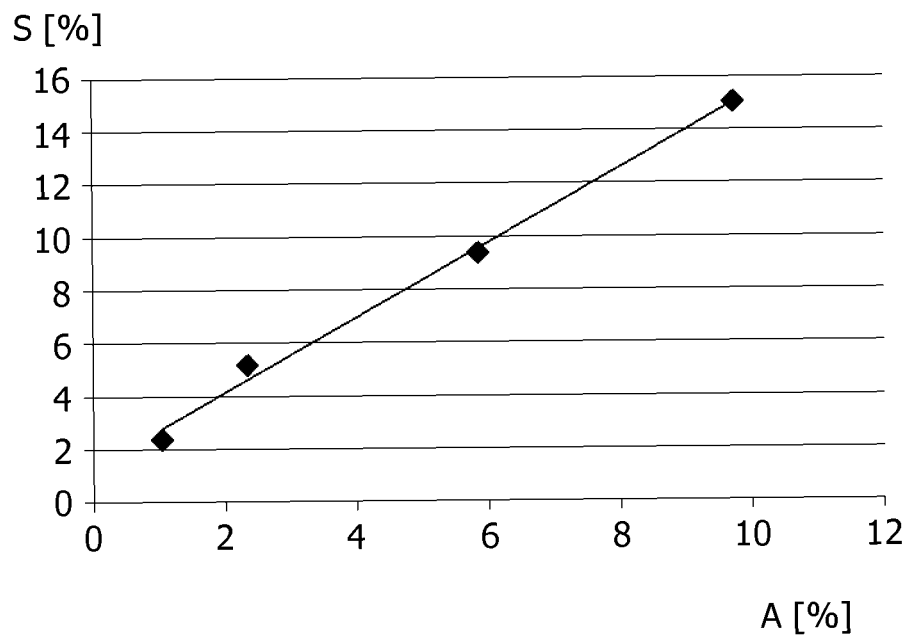
FIG. 12 shows the correlation between the observed FTIR signal change S in the target region and the amplitude A of the signal for 100 pM cTnI determinations using different particle amounts M in the assay.

FIG. 12 shows that FIGS. 8 and 11 can be combined to show the relationship between the signal change S measured in the target region TR and the signal amplitude A (measured e.g. in the reference region(s) RR) for 100 pM cTnI determinations using different amounts of magnetic particles in the assay.

Figure 13:
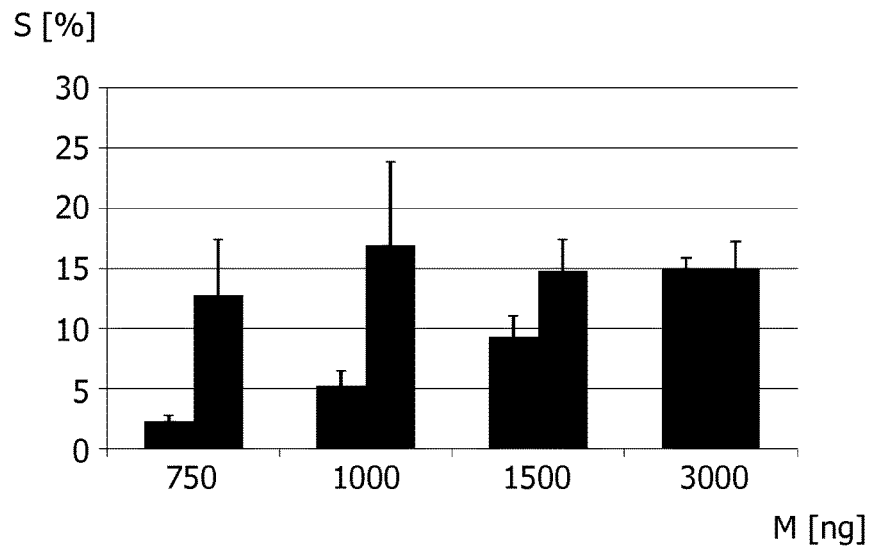
FIG. 13 shows FTIR signal changes S of 100 pM cTnI measurements using different particle amounts M, both uncorrected (left bars) and corrected using amplitudes (right bars)

From such a determined correlation, the measured signal change S can be corrected. This is illustrated in FIG. 13, which shows signal changes S of 100 pM cTnI measurements using different amounts M of magnetic particles, both uncorrected (left bars) and corrected (right bars) using the simultaneously measured amplitude A.

If desired, the accuracy of the corrected measurements can be further improved for example by using different signal processing, using more reference regions etc. Another improvement may be based on the observation that the signal obtained in a measurement (e.g. FTIR, single bead measurements, scattered light measurement etc.) at any given point in time is directly proportional to the amount of particles having a close interaction with the surface at that time. Therefore in principle, summing up all the signal obtained in an assay is proportional to the total amount of particles that have interacted with the surface during that assay. The accuracy of the measurements may thus be improved by correcting for the total amount of observed interactions (the cumulative signal change).

Another aspect that can be addressed with the sensor device 200 is the problem of magnetic particle clustering. In short, sample fluids like human plasma seem to contain interfering factors that cause the irreversible aggregation ("clustering") of the magnetic particles, which leads to a decreased assay performance.

Figure 14:
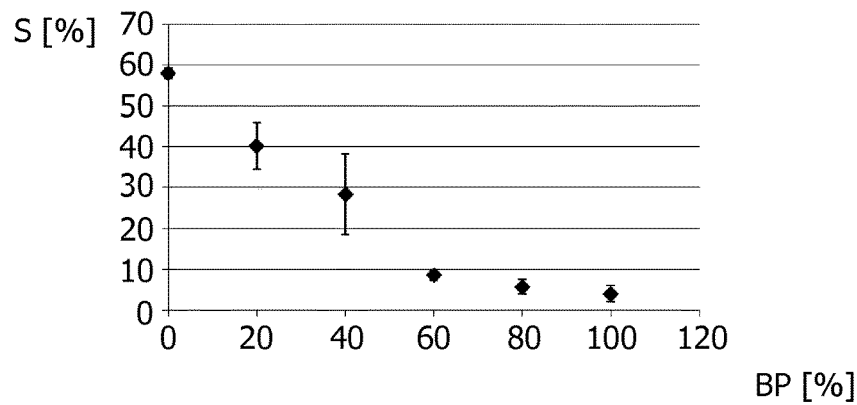
FIG. 14 shows FTIR signal changes S obtained for the detection of 250 pM cTnI in samples exhibiting different degrees BP of clustering.

This is illustrated in FIG. 14, which shows the (endpoint) signal change S obtained in the target region for the detection of 250 pM cTnI in samples exhibiting different degrees BP of (irreversible) clustering. Said samples were obtained by mixing a first plasma displaying a high degree of clustering with a second plasma displaying no clustering, wherein the value BP represents the relative amount of the first plasma. The diagram clearly shows that the signal change S decreases with increasing degree BP of clustering.

Even if measures are taken to avoid irreversible clustering of magnetic particles, there may still be some clustering present in the final sample, for example due to extended storage of the magnetic particles in a dry format. A way of accurately determining an "auxiliary parameter" that is related to the amount of clustering in a magnetic particle assay would therefore be valuable.

Figure 15:
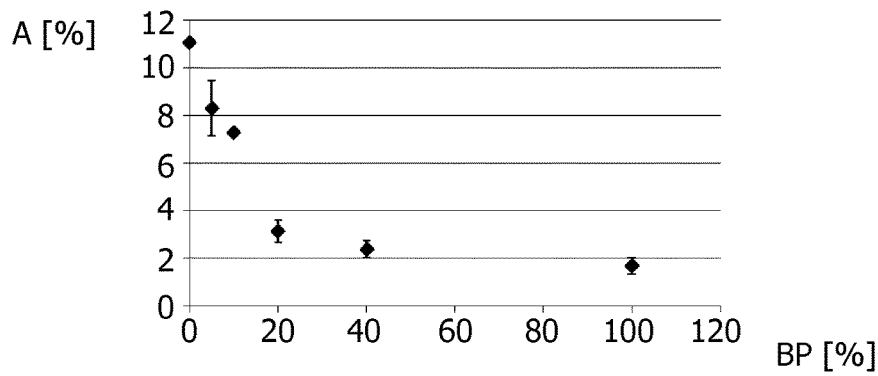
FIG. 15 shows signal amplitudes A obtained for the detection of 250 pM cTnI in samples exhibiting different degrees of clustering.

The diagram of FIG. 15 indicates a way how the aforementioned auxiliary parameter can be achieved. The diagram shows the signal amplitude A (as defined above, cf. FIGS. 7, 9, 10) measured for 250 pM cTnI samples in a reference region in dependence on the degree BP of clustering (said degree being determined as in FIG. 14). From this diagram it can be concluded that the variations of the raw FTIR signal R(t) also contain information about the aggregation state of the particles in an assay. Hence the signal amplitude A (or a value derived therefrom) can be used as the desired auxiliary parameter indicating the degree of clustering.

Figure 16:
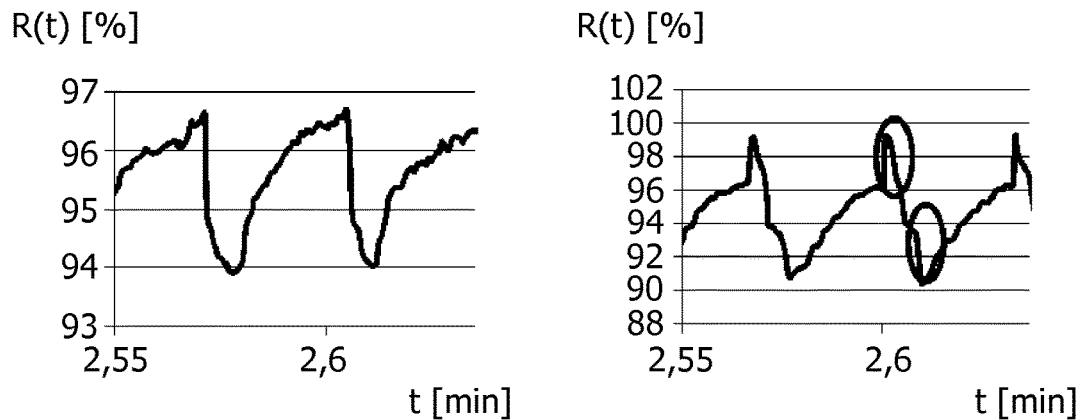
FIG. 16 shows the FTIR detection signal shape obtained in samples exhibiting plasma with high degree of clustering (left diagram) and plasma without clustering (right diagram)

Another approach to determine an auxiliary parameter related to the aggregation state of magnetic particles is illustrated in FIG. 16. In the left diagram of this Figure, pulses of the (raw) signal R(t) obtained in samples exhibiting plasma with high degree of clustering are shown in high temporal resolution. In the right diagram, corresponding pulses of R(t) are shown that were obtained in samples without clustering. Comparison of the diagrams reveals that the presence of the sharp peaks (right diagram) during switching between attractive part of the magnetic field pulse and the part of free diffusion of the beads indicates that a sample is cluster-free and beads are monodisperse. Absence of above-mentioned peaks, on the contrary, is a sign of the bead clustering (left diagram). An associated "auxiliary parameter" can hence be defined as the degree such peaks are expressed in the curves of the measurement signal R(t) (such a degree can e.g. be automatically calculated by suitable feature detection software).

Figure 17:
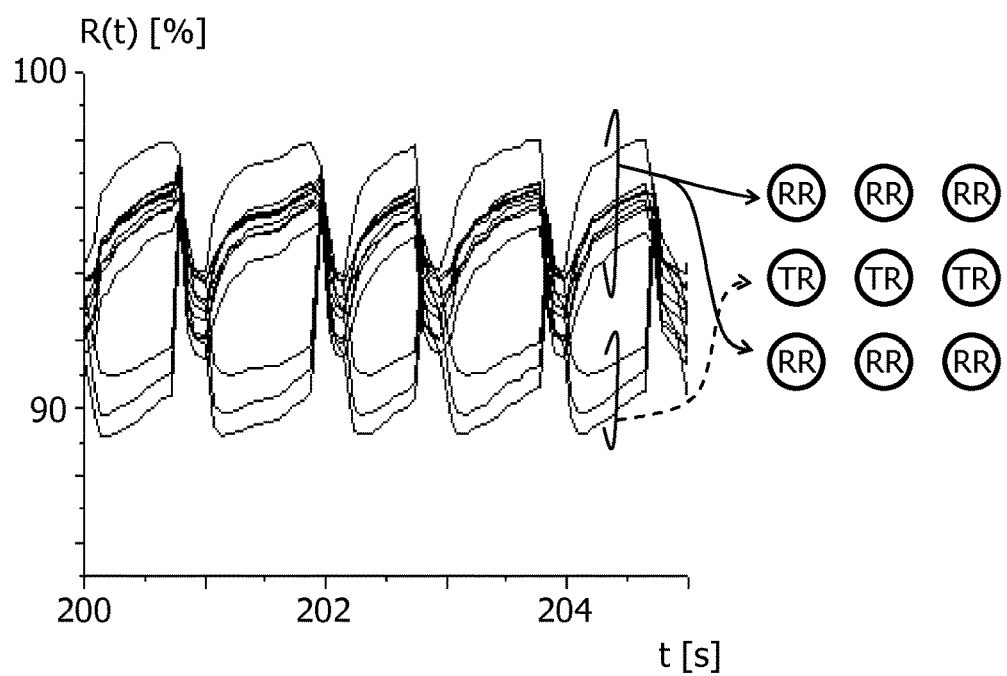
FIG. 17 shows FTIR detection signals S obtained in three parallel rows of detection regions.

The diagram of FIG. 17 shows the variation of the (raw) signals R(t) over time t for six reference regions RR and three target regions TR that are arranged as indicated on the right side of the diagram. The example shows a case in which the cartridge (detection area) was positioned in such a way that homogeneous bead distribution over the surface was achieved. The symmetry of the magnetic field is evident from the comparable signals of the bottom and top rows of reference regions RR. Although the signals from the middle row of target regions TR are different from the bottom and top rows at a given moment in time, on average, the interaction of the beads is the same for all detection regions (for which the actuation protocol was especially designed). According to this diagram, the determination of an auxiliary parameter that is related to the homogeneity/symmetry of the magnetic field can be achieved from the comparison of signals R(t) obtained in spatially distributed detection regions.

Returning to FIG. 7, attention is drawn to the line G that indicates the initial slope of the signal R(t) during the up-concentration phase b). It is known that the viscosity $\eta$ of a sample is determined by the formula $$\eta = \frac{1}{6 \cdot \pi \cdot D \cdot V} \cdot X \cdot \nabla \left[ \frac{B^2}{\mu_0} \right] = \frac{1}{6 \cdot \pi \cdot D \cdot V} \cdot F_{mag},$$

wherein D is the average diameter of the magnetic particles, $F_{mag}$ is magnetic force exerted by the magnetic field B, $\chi$ is the magnetic susceptibility of the beads, and V is the velocity of the beads. The velocity V of the beads is directly proportional to the change of the signal R(t) within the first few seconds, i.e. to the slope G=$\Delta$R/$\Delta$t. Hence it turns out that the slope G can serve as an auxiliary parameter which provides information about the viscosity $\eta$ of the sample.

In summary, it was described how different kinds of information can be extracted from the signals obtained during an assay using actuated magnetic particles and frustrated total internal reflection detection. This information can be used e.g. as a control, to disqualify a measurement if one aspect of the measurement is deviating from an expected value (e.g. when the amount of particles in a cartridge is incorrect). Furthermore, if it is known how this deviation effects the assay result, the information can be used as a calibrator, to correct the obtained signal change.

While the invention was described above with reference to particular embodiments, various modifications and extensions are possible, for example:

The sensor device can comprise any suitable sensor to detect the presence of magnetic particles on or near to a sensor surface, based on any property of the particles, e.g. it can detect via magnetic methods (e.g. magnetoresistive, Hall, coils), optical methods (e.g. imaging, fluorescence, chemiluminescence, absorption, scattering, evanescent field techniques, surface plasmon resonance, Raman, etc.), sonic detection (e.g. surface acoustic wave, bulk acoustic wave, cantilever, quartz crystal etc), electrical detection (e.g. conduction, impedance, amperometric, redox cycling), combinations thereof, etc.

In addition to molecular assays, also larger moieties can be detected with sensor devices according to the invention, e.g. cells, viruses, or fractions of cells or viruses, tissue extract, etc.

The detection can occur with or without scanning of the sensor element with respect to the sensor surface.

Measurement data can be derived as an end-point measurement, as well as by recording signals kinetically or intermittently.

The particles serving as labels can be detected directly by the sensing method. As well, the particles can be further processed prior to detection. An example of further processing is that materials are added or that the (bio)chemical or physical properties of the label are modified to facilitate detection.

The device and method can be used with several biochemical assay types, e.g. binding/unbinding assay, sandwich assay, competition assay, displacement assay, enzymatic assay, etc. It is especially suitable for DNA detection because large scale multiplexing is easily possible and different oligos can be spotted via ink-jet printing on a substrate.

The device and method are suited for sensor multiplexing (i.e. the parallel use of different sensors and sensor surfaces), label multiplexing (i.e. the parallel use of different types of labels) and chamber multiplexing (i.e. the parallel use of different reaction chambers).

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:
1. A sensor device for the detection of magnetic particles in a sample chamber with a contact surface at which magnetic particles can collect, comprising:
  a) a sensor unit for detecting magnetic particles in a target region on the contact surface and/or in at least one reference region on the contact surface;
  b) a magnetic field generator for generating a magnetic field that guides magnetic particles to the contact surface; and
  c) an evaluation unit for determining from the detection signals of the sensor unit an auxiliary parameter that is related to the magnetic particles and/or their movement but that is independent of binding processes taking place in the target region between magnetic particles and the contact surface;
wherein the magnetic field generator is configured to guide magnetic particles to the target region, and
wherein the auxiliary parameter measures a degree of a mismatch between the positions reached by the magnetic particles and the target region.

2. The sensor device according to claim 1, wherein:
at least one reference region is disposed outside the target region, and/or
at least one reference region overlaps with the target region.

3. The sensor device according to claim 1,
wherein the sample chamber is disposed in an exchangeable cartridge.

4. The sensor device according to claim 1,
wherein the target region comprises a binding region with binding sites for the magnetic particles.

5. The sensor device according to claim 1,
wherein the auxiliary parameter is related to:
  a) the amount of magnetic particles in the sample chamber,
  b) a clustering of magnetic particles,
  c) the viscosity of the medium in the sample chamber,
  d) the generated magnetic field,
  e) the redispersion condition of magnetic particles, and/or
  f) the spatial distribution of magnetic particles.

6. The sensor device according to claim 1,
wherein the magnetic field that guides the magnetic particles is pulsed.

7. The sensor device according to claim 6,
wherein the auxiliary parameter is determined from detection signals recorded during the action of the modulated magnetic field.

8. The sensor device according to claim 7,
wherein the auxiliary parameter is determined from the local amplitudes of the recorded detection signals and/or from the shape of pulses of the recorded detection signals.

9. The sensor device according to claim 1,
wherein the auxiliary parameter is determined from the rate of change of the recorded detection results.

10. The sensor device according to claim 1,
wherein an alarm signal is generated if the auxiliary parameter is outside a given a range.

11. The sensor device according to claim 1,
wherein detection results for the target region are corrected according to the auxiliary parameter.

12. The sensor device according to claim 1,
wherein the sensor unit is further for detecting magnetic particles with an optical, magnetic, mechanical, acoustic, thermal or electrical sensor element.

13. The sensor device according to claim 1,
wherein the auxiliary parameter is related to at least three of:
  a) the amount of magnetic particles in the sample chamber,
  b) a clustering of magnetic particles,
  c) the viscosity of the medium in the sample chamber,
  d) the generated magnetic field,
  e) the redispersion condition of magnetic particles, and
  f) the spatial distribution of magnetic particles.

14. The sensor device according to claim 1,
wherein the auxiliary parameter is related to:
  a) the amount of magnetic particles in the sample chamber,
  b) a clustering of magnetic particles,
  c) the viscosity of the medium in the sample chamber,
  d) the generated magnetic field,
  e) the redispersion condition of magnetic particles, and
  f) the spatial distribution of magnetic particles.

15. The sensor device according to claim 1,
wherein the auxiliary parameter is determined from a comparison of the detection results in the target region and in at least one reference region.

16. The sensor device according to claim 1,
wherein the degree of mismatch is expressed as a percentage of the magnetic particles not reaching the target region.

17. A sensor device for the detection of magnetic particles in a sample chamber with a contact surface at which magnetic particles can collect, comprising:
  a) a sensor unit for detecting magnetic particles in a target region on the contact surface and/or in at least one reference region on the contact surface;
  b) a magnetic field generator for generating a magnetic field that guides magnetic particles to the contact surface; and
  c) an evaluation unit for determining from the detection signals of the sensor unit an auxiliary parameter that is related to the magnetic particles and/or their movement but that is independent of binding processes taking place in the target region between magnetic particles and the contact surface;
wherein:
  there are at least two reference regions disposed at different sides of the target region, and
  the detection signals obtained from these reference regions are individually evaluated with respect to a possible clustering of magnetic particles.

18. A sensor device for the detection of magnetic particles in a sample chamber with a contact surface at which magnetic particles can collect, comprising:
  a) a sensor unit for detecting magnetic particles in a target region on the contact surface and/or in at least one reference region on the contact surface;
  b) a magnetic field generator for generating a magnetic field that guides magnetic particles to the contact surface; and
  c) an evaluation unit for determining from the detection signals of the sensor unit an auxiliary parameter that is related to the magnetic particles and/or their movement but that is independent of binding processes taking place in the target region between magnetic particles and the contact surface;
wherein:
  at least one reference region is disposed outside the target region, and
  at least one reference region overlaps with the target region.

* * * * *